United States Patent
Tani et al.

(10) Patent No.: US 11,890,372 B2
(45) Date of Patent: Feb. 6, 2024

(54) TRANSFUSION PREPARATION

(71) Applicant: OTSUKA PHARMACEUTICAL FACTORY, INC., Naruto (JP)

(72) Inventors: Seiji Tani, Naruto (JP); Seiji Fujita, Naruto (JP); Teru Nakai, Naruto (JP); Yasuhiro Kiuchi, Naruto (JP); Miyuki Yamanaka, Naruto (JP); Yui Hayashi, Naruto (JP); Hiroshi Kanno, Naruto (JP); Yu Saruwatari, Naruto (JP)

(73) Assignee: OTSUKA PHARMACEUTICAL FACTORY, INC., Naruto (JP)

( * ) Notice: Subject to any disclaimer, the term of this patent is extended or adjusted under 35 U.S.C. 154(b) by 0 days.

(21) Appl. No.: 16/980,201

(22) PCT Filed: Mar. 13, 2019

(86) PCT No.: PCT/JP2019/010195
§ 371 (c)(1),
(2) Date: Sep. 11, 2020

(87) PCT Pub. No.: WO2019/176996
PCT Pub. Date: Sep. 19, 2019

(65) Prior Publication Data
US 2021/0007975 A1     Jan. 14, 2021

(30) Foreign Application Priority Data
Mar. 13, 2018 (JP) ................. 2018-045822

(51) Int. Cl.
| | | |
|---|---|---|
| *A61K 9/00* | (2006.01) | |
| *A23L 33/175* | (2016.01) | |
| *A23L 33/115* | (2016.01) | |
| *A23L 33/16* | (2016.01) | |
| *A61J 1/20* | (2006.01) | |
| *A61K 9/107* | (2006.01) | |
| *A61K 35/57* | (2015.01) | |
| *A61K 36/48* | (2006.01) | |
| *A61K 47/02* | (2006.01) | |
| *A61K 47/12* | (2006.01) | |
| *A61K 47/18* | (2017.01) | |
| *A61K 47/20* | (2006.01) | |
| *A61K 47/22* | (2006.01) | |

(52) U.S. Cl.
CPC .......... *A61K 9/0029* (2013.01); *A23L 33/115* (2016.08); *A23L 33/16* (2016.08); *A23L 33/175* (2016.08); *A61J 1/2093* (2013.01); *A61K 9/107* (2013.01); *A61K 35/57* (2013.01); *A61K 36/48* (2013.01); *A61K 47/02* (2013.01); *A61K 47/12* (2013.01); *A61K 47/183* (2013.01); *A61K 47/20* (2013.01); *A61K 47/22* (2013.01); *A23V 2002/00* (2013.01)

(58) Field of Classification Search
CPC ....... A61K 9/0029; A61K 9/10; A23L 33/175; A23L 33/115; A23L 33/16; A61J 1/2093
See application file for complete search history.

(56) References Cited

U.S. PATENT DOCUMENTS

| | | |
|---|---|---|
| 5,693,337 A | 12/1997 | Suzuki et al. |
| 5,993,863 A | 11/1999 | Kikuchi et al. |
| 9,446,184 B2 | 9/2016 | Tani et al. |
| 9,687,600 B2 | 6/2017 | Tani et al. |
| 9,884,149 B2 | 2/2018 | Tani et al. |
| 2013/0313261 A1 | 11/2013 | Tani et al. |
| 2016/0101231 A1 | 4/2016 | Tani et al. |
| 2017/0304530 A1 | 10/2017 | Tani et al. |

FOREIGN PATENT DOCUMENTS

| | | |
|---|---|---|
| EP | 0510687 A2 | 10/1992 |
| EP | 0998935 A1 | 5/2000 |
| JP | H8-081360 A | 3/1996 |
| JP | H11-343229 A | 12/1999 |
| JP | 2001-79064 A | 3/2001 |
| JP | 2001-328934 A | 11/2001 |
| WO | 94/025059 A1 | 11/1994 |
| WO | 2012/073891 A1 | 6/2012 |

OTHER PUBLICATIONS

International Search Report for PCT/JP2019/010195 dated May 21, 2019 (PCT/ISA/210).
Extended European Search Report dated Nov. 25, 2021 in corresponding European Application No. 19767271.0.

*Primary Examiner* — Brian J. Sines
(74) *Attorney, Agent, or Firm* — Sughrue Mion, PLLC

(57) ABSTRACT

The present invention provides an infusion preparation that is inhibited from generation of unwanted insoluble matter after mixing of two liquids of the infusion preparation in long-term storage. More specifically, the present invention provides an infusion preparation comprising two chambers separated by a communicably openable partition, a first chamber containing a first-chamber infusion comprising a fat emulsion and further comprising at least one member selected from the group consisting of amino acids that have a buffer action, divalent organic acids, and trivalent organic acids, a second chamber containing a second-chamber infusion comprising an amino acid and at least calcium as an electrolyte, wherein a total concentration of the amino acids that have a buffer action, divalent organic acids, and trivalent organic acids in the first-chamber infusion is 0.15 to 0.5 g/L, and a mixture of the first- and second-chamber infusions has a pH of 6.53 or less as measured 48 hours after the partition is communicably opened.

6 Claims, No Drawings

TRANSFUSION PREPARATION

CROSS REFERENCE TO RELATED APPLICATIONS

This application is a National Stage of International Application No. PCT/JP2019/010195 filed Mar. 13, 2019, claiming priority based on Japanese Patent Application No. 2018-045822 filed Mar. 13, 2018.

TECHNICAL FIELD

The present invention relates to an infusion preparation comprising a fat, an amino acid, and an electrolyte. More specifically, the present invention provides an infusion preparation, which is an infusion preparation contained in a two-chamber container, wherein a first chamber contains a sugar and a fat emulsion, and a second chanter contains an amino acid and an electrolyte.

BACKGROUND ART

As an infusion preparation for parenteral nutrition (PN), there is proposed an infusion preparation (an intravenous nutrient infusion preparation) comprising two chambers separated by a communicably openable partition, wherein a first chamber contains a first-chamber infusion comprising a sugar and a fat emulsion, and a second chamber contains a second-chamber infusion comprising an amino acid and an electrolyte (Patent Literature (PTL) 1).

These infusion preparations are used, for example, for peripheral parenteral nutrition (PPN) and central parenteral nutrition (TPN) methods.

These infusion preparations are transported to facilities of use, such as hospitals, through distribution and sale after production, and are stored in the facilities until the infusion preparations are actually used clinically. These infusion preparations are required to be stable during the period from production, to clinical use. The stability of an infusion preparation is usually ensured by testing and clarifying the period during which stability can be guaranteed, and setting the expiration date for use of the infusion preparation so as not to exceed the stability guarantee period.

CITATION LIST

Patent Literature

PTL 1: WO2012/073891

SUMMARY OF INVENTION

Technical Problem

Through their own investigation, the present inventors found out that when an intravenous nutrient infusion preparation is left for a certain period of time after production, unwanted insoluble matter may be observed in a mixture of a first-chamber infusion and a second-chamber infusion after a partition between first and second chambers is opened to allow for communication.

An object of the present invention is to provide an infusion preparation that is inhibited from generation of unwanted insoluble matter after mixing two liquids of the infusion preparation in long-term storage.

Solution to Problem

Through their own investigation, the present inventors elucidated the cause of generation of such unwanted insoluble matter after mixing two liquids. The inventors clarified that, free fatty acids are formed in a first-chamber infusion during long-term storage, and unwanted insoluble matter is generated after mixing two liquids due to the presence of such free fatty acids. Based on this finding, the inventors repeated trial and error, and found that when a first-chamber infusion comprises at least one member selected from the group consisting of amino acids that have a buffer action, divalent organic acids, and trivalent organic acids in a concentration of 0.15 g/L or more, formation of free fatty acids in the first-chamber infusion during long-term storage can be inhibited. The inventors further found that if a mixture of first- and second-chamber infusions formed after a partition between first and second chambers is opened to allow for communication has a pH of 6.53 or less, generation of unwanted insoluble matter, which would occur due to the presence of such free fatty acids after mixing two liquids, can be inhibited.

The present invention has been accomplished with further improvements, and includes the following embodiments.

Item 1.

An infusion preparation comprising two chambers separated by a communicably openable partition,
- a first chamber containing a first-chamber infusion comprising a fat emulsion and further comprising at least one member selected from the group consisting of amino acids that have a buffer action, divalent organic acids, and trivalent organic acids,
- a second chamber containing a second-chamber infusion comprising an amino acid and at least calcium as an electrolyte, wherein
- a total concentration of the amino acids that have a buffer action, divalent organic acids, and trivalent organic acids in the first-chamber infusion is 0.15 to 0.5 g/L, and
- a mixture of the first- and second-chamber infusions has a pH of 6.53 or less as measured 48 hours after the partition is communicably opened.

Item 2.

The infusion preparation according to Item 1, wherein the fat emulsion comprises an emulsifying agent, and the first-chamber infusion comprises the emulsifying agent in a concentration of 0.01 to 2 w/v %.

Item 3.

The infusion preparation according to Item 1 or 2, wherein the mixture of the first- and second-chamber infusions after the partition is communicably opened contains $Ca^{2+}$ in a concentration of 1 mEq/L or more.

Item 4.

The infusion preparation according to any one of Items 1 to 3, wherein the second-chamber infusion further comprises at least citric acid as the electrolyte, and the second-chamber infusion has a citric acid concentration (mEq) equal to or more than the calcium concentration (mEq).

Item 5.

The infusion preparation according to any one of Items 1 to 4, wherein the first-chamber infusion comprises at least histidine as the amino acids that have a buffer action.

Item 6.

A mixture of the first- and second-chamber infusions of any one of Items 1 to 5 obtained by communicably opening the partition.

Advantageous Effects of Invention

The infusion preparation of the present invention is inhibited from generation of unwanted insoluble matter after mixing two liquids in long-term storage. Therefore, the usable period of the infusion preparation can be set longer.

The present invention is described below in more detail.

The present invention provides an infusion preparation comprising two chambers separated by a communicably openable partition, a first chamber containing a first-chamber infusion comprising a fat emulsion, a second chamber containing a second-chamber infusion comprising an amino acid and an electrolyte.

First-Chamber Infusion

The first-chamber infusion used in the present invention comprises a fat emulsion and further comprises at least one member selected from the group consisting of amino acids that have a buffer action, divalent organic acids, and trivalent organic acids.

The fat emulsion incorporated in the first-chamber infusion is an oil-in-water emulsion that is produced by dispersing an oil and/or fat in water by using an emulsifying agent. The fat emulsion can be produced according to a usual method. For example, the fat emulsion can be produced by adding an oil and/or fat, and an emulsifying agent to water, stirring the mixture to prepare a crude emulsion, and emulsifying the crude emulsion by a conventional method, such as a high-pressure emulsification method.

The oil and/or fat is preferably edible oil. Specific examples include vegetable oils (e.g., soybean oil, olive oil, cottonseed oil, safflower oil, corn oil, coconut oil, and perilla oil); fish oils (e.g., sardine oil); medium-chain fatty acid triglycerides ($C_{8-10}$ fatty acid triglycerides) (e.g., product names: PANACET (produced by NOF Corporation), ODO (produced by Nisshin Oil Mills, Ltd.), COCONARD (produced by Kao Corporation), and Miglyol (produced by Mitsuba Trading Co., Ltd.)); synthetic triglycerides (e.g., 2-linoleoyl-1,3-dioctanoyl glycerol (8L8) and 2-linoleoyl-1,3-didecanoyl-glycerol (10L10)); and the like. Such oils and fats may be used singly or in a combination of two or more.

The emulsifying agent may be selected from, for example, various pharmaceutically acceptable emulsifying agents. Specific examples include egg yolk phospholipid (egg yolk lecithin), hydrogenated egg yolk phospholipid, soybean phospholipid (soybean lecithin), hydrogenated soybean phospholipid, nonionic surfactants, and the like. Such emulsifying agents may be used singly or in a combination of two or more.

The oil and/or fat is particularly preferably soybean oil. The emulsifying agent is particularly preferably egg yolk phospholipid (egg yolk lecithin). Lecithin, such as egg yolk lecithin, is preferable because it can also act as a phosphorus source as described below.

Insofar as an oil-in-water fat emulsion is produced, the amounts of oil and/or fat and emulsifying agent used to prepare the fat emulsion are not particularly limited. The oil and/or fat is preferably used in such an amount as to achieve a concentration of about 0.5 to 6 w/v %, and more preferably about 1 to 5 w/v % in the obtained fat emulsion. Furthermore, the emulsifying agent is preferably used in such an amount as to achieve a concentration of about 0.01 to 2 w/v %, more preferably about 0.1 to 1.5 w/v %, and still more preferably about 0.2 to 1.5 w/v % in the obtained fat emulsion. The concentration of the emulsifying agent in the first-chamber infusion within this range can, together with other features of the present invention, inhibit the formation of free fatty acids during long-term storage, thereby inhibiting the generation of unwanted insoluble matter after mixing the two liquids in long-term storage.

One specific example of a particularly preferable method for producing the fat emulsion according to the present invention is described below. Specifically, an oil and/or fat and an emulsifying agent are added to water, and at least one member selected from glycerol and glucose is added thereto. The mixture is then stirred to prepare a crude emulsion. Subsequently, the crude emulsion is emulsified by a conventional method, such as a high-pressure emulsification method. The high-pressure emulsification method may be carried out, for example, by passing the crude emulsion through an emulsifier, such as a Manton Gaulin homogenizer, at a rate of 20 to 700 kg/cm$^2$ about 2 to 50 times, and preferably 3 to 20 times. In this method, insofar as glycerol and/or glucose is present during the emulsification, how and when they are added are not limited. For example, glycerol and/or glucose may be added to the crude emulsion prepared by using an oil and/or fat and an emulsifying agent, and the resulting crude emulsion may be emulsified. The obtained fat emulsion contains glycerol and/or glucose in a concentration of preferably about 5 to 70 w/v %, and more preferably about 10 to 30 w/v %.

The first-chamber infusion further comprises at least one member selected from the group consisting of amino acids that have a buffer action, divalent, organic acids, and trivalent organic acids. In the first-chamber infusion, the total, concentration of the amino acids that have a buffer action, divalent organic acids, and trivalent organic acids is 0.15 to 0.5 g/L. The total concentration of the amino acids that have a buffer action is calculated based on the amount of these amino acids as free amino acids. Without, being bound by theory, the study of the present inventors suggests that free fatty acids are formed by decomposition of an oil and/or fat or an emulsifier during long-term storage, and it has also been revealed that the degree of the formation by decomposition depends on pH. Further, a reduction in pH accompanied by the formation of free fatty acids presumably further promotes the formation of free fatty acids. Therefore, to inhibit the generation of unwanted insoluble matter after mixing of the two liquids, it appeared to be important to maintain the pH of the first-chamber infusion within an optimal range. To achieve this, it is considered to be important to enhance the buffer action of the first-chamber infusion at a pH within the optimal range to thus maintain the pH of the first-chamber infusion within this optimal range. The optimal pH range that can prevent an oil and/or fat and an emulsifier from being decomposed to form free fatty acids etc. is preferably 4.5 to 6.5, more preferably 5.0 to 6.5, and still more preferably 5.5 to 6.5.

The amino acids that have a buffer action are not particularly limited insofar as they are capable of enhancing the buffer action of the first-chamber infusion at the pH range in which an oil and/or fat and an emulsifier are prevented from being decomposed to form free fatty acids etc. to thus allow the pH of the first-chamber infusion to be within the above range. Examples include histidine, lysine, arginine, and the like. The presence of the amino acids that have a buffer action can prevent an oil and/or fat and an emulsifying agent from being decomposed to form free fatty acids etc., and suppress a reduction of the pH of the second-chamber infusion over time. Such amino acids that have a buffer action are preferably L-histidine and L-lysine, and more preferably L-histidine. The amino acids that have a buffer action furthermore preferably consist substantially only of L-histidine or consist of only L-histidine. Histidine also functions as a pH adjuster.

The divalent organic acids and trivalent organic acids are not particularly limited insofar as they are capable of enhancing the buffer action of the first-chamber infusion at the pH range in which an oil and/or fat and an emulsifier are prevented from being decomposed to form free fatty acids etc. to thus allow the pH of the first-chamber infusion to be within the above range. Examples include citric acid, succinic acid, malic acid, tartaric acid, and the like. The presence of the divalent organic acids or trivalent organic acids can prevent an oil and/or fat and an emulsifying agent from being decomposed to form free fatty acids etc., and suppress a reduction of the pH of the second-chamber infusion over time. Citric acid, succinic acid, malic acid, and tartaric acid also function as a pH adjuster.

When the first-chamber infusion comprises at least one member selected from the group consisting of amino acids that have a buffer action, divalent organic acids, and trivalent organic acids in a total concentration of 0.15 g/L or more, the formation of free fatty acids in the first-chamber infusion is inhibited during long-term storage, whereby the generation of unwanted insoluble matter is inhibited after mixing of the two liquids in long-term storage. To achieve this effect, the first-chamber infusion preferably comprises the at least one member selected from the group consisting of amino acids that have a buffer action, divalent organic acids, and trivalent organic acids in a total concentration of 0.2 g/L or more. In the first-chamber infusion, the upper limit of the total concentration of the at least one member selected from the group consisting of amino acids that have a buffer action, divalent organic acids, and trivalent organic acids is for example, 0.6 g/L, and preferably 0.5 g/L. The total concentration of the at least one member selected from the group consisting of amino acids that have a buffer action, divalent organic acids, and trivalent organic acids, contained in the first-chamber infusion is preferably within this range, in view of an actual performance as a pharmaceutical additive and prevention of discoloration when a reducing sugar, such as glucose, is incorporated. To summarize the above, the first-chamber infusion comprises the at least one member selected from the group consisting of amino acids that have a buffer action, divalent organic acids, and trivalent organic acids in a total concentration of preferably 0.15 to 0.6 g/L, and more preferably 0.2 to 0.3 g/L.

Further, various known additives that can be added to fat emulsions may be also optionally incorporated. Examples of such additives include pH adjusters. The pH adjusters may be those that are known to be used in infusion preparations. For example, organic acids and amino acids may be used, in addition to acids such as hydrochloric acid, and alkalis such as sodium hydroxide and potassium hydroxide. Examples of organic acids include acetic acid, lactic acid, and the like. Examples of amino acids include L-lysine and the like. Among these, oil-soluble materials may be mixed in advance with oily components of the emulsion, while water-soluble materials may be mixed with water for injection, or may be added to the aqueous phase of the obtained fat emulsion. The amounts of additives can be suitably determined, and may be, for example, the same as conventionally known amounts.

The first-chamber infusion comprises fat emulsion in a concentration of, for example, 0.5 to 6 w/v %, preferably 1 to 5 w/v %, and more preferably 2 to 5 w/v %, based on the amount of oils and fats. In the infusion preparation of the present invention, the mixture of the first- and second-chamber infusions comprises fat emulsion in a concentration of, for example, 0.25 to 6 w/v %, preferably 0.5 to 3 w/v %, and more preferably 1 to 2.5 w/v %, based on the amount of oils and fats.

The first-chamber infusion preferably has a pH of 4.5 to 6.5, more preferably 5.0 to 6.5, and still more preferably 5.5 to 6.5. When the pH is within this range, it is possible to prevent an oil/and fat and an emulsifier from being decomposed to form free fatty acids etc., and to stabilize the fat emulsion and vitamin $B_1$ in the first-chamber infusion. The pH of the first-chamber infusion can be adjusted by using a pH adjuster. L-histidine, L-arginine, malic acid, citric acid, succinic acid, tartaric acid, etc., mentioned earlier, may be used as a pH adjuster. It is also possible to use hydrochloric acid, acetic acid, lactic acid, sodium hydroxide, potassium hydroxide, etc. as a pH adjuster.

The first-chamber infusion preferably comprises a sugar. Examples of sugars that can be incorporated include reducing sugars such as glucose/fructose, and maltose; non-reducing sugars such as xylitol, sorbitol, and glycerol; and the like. Among these sugars, a reducing sugar is preferably incorporated in the first-chamber infusion, and glucose is more preferably incorporated from the viewpoint of blood glucose level management etc. Such sugars may be used singly or in a combination of two or more.

The first-chamber infusion comprises a sugar in a concentration of preferably 70 to 150 g/L. Further, the mixture of the first- and second-chamber infusions obtained by communicably opening the partition preferably has a sugar concentration of 50 to 100 g/L, and more preferably 50 to 75 g/L.

To prevent the onset of acidosis during infusion therapy, vitamin $B_1$ is preferably incorporated in the first-chamber infusion. Examples of vitamin $B_1$ that can be incorporated in the first-chamber infusion include thiamine chloride hydrochloride, thiamine mononitrate, prosultiamine, octotiamine, and the like.

The first-chamber infusion comprises vitamin $B_1$ in a concentration of, for example, 1.5 to 10 mg/L, and preferably 2 to 8 mg/L, based on the thiamine amount. In the infusion preparation of the present invention, the mixture of the first- and second-chamber infusions obtained by communicably opening the partition preferably has a vitamin $B_1$ concentration of 1 to 6 mg/L, and more preferably 1.5 to 4 mg/L, based on the thiamine amount.

In view of further enhancing the stability of vitamin $B_1$, the first-chamber infusion preferably has a titratable acidity of 10 or less. The titratable acidity refers to an amount (mL) of a 0.1 mol/L sodium hydroxide aqueous solution required to neutralize 100 ml of a solution to pH 7.4.

Distilled water for injection can be typically used as a solvent of the first-chamber infusion.

In the infusion preparation of the present invention, the fluid volume of the first-chamber infusion is suitably determined according to, for example, the total fluid volume of the infusion preparation or the fluid volume of the second-chamber infusion.

The first-chamber infusion may be substantially free of potassium. The phrase "substantially free of potassium" means that no potassium-containing compounds are added. Further, the first-chamber infusion is preferably substantially free of calcium. The phrase "substantially free of calcium" means that no calcium-containing compounds are added.

The first-chamber infusion has a relative osmotic pressure of 2.0 to 4.0, and preferably about 2.0 to 3.5. The relative osmotic pressure as used herein refers to a ratio relative to the osmotic pressure of physiological saline (i.e., a relative ratio with the osmotic pressure of physiological saline defined as 1). The relative osmotic pressure of the infusion refers to a ratio relative to the osmotic pressure of physiological saline unless otherwise specified.

Second-Chamber Infusion

The second-chamber infusion used in the present invention comprises an amino acid and calcium as an electrolyte.

The amino acids incorporated in the second-chamber infusion are not limited as long as they can be incorporated in amino acid infusions for nutritional supplementation for the body. In the present invention, the amino acids are typically used in the form of a free amino acid. However, amino acids in the form of a pharmaceutically acceptable salt, an eater, a N-acyl derivative, or a dipeptide may also be used. Specific examples of free amino acids that can be incorporated in the second-chamber infusion include L-leucine, L-isoleucine, L-valine, L-lysine, L-threonine, L-tryptophan, L-methionine, L-phenylalanine, L-cysteine, L-tyrosine, L-arginine, L-histidine, L-alanine, L-proline, L-serine, glycine, L-aspartic acid, L-glutamic acid, and the like. Specific examples of amino acid salts include inorganic acid salts such as L-arginine hydrochloride, L-cysteine hydrochloride, L-glutamic acid hydrochloride, L-histidine hydrochloride, and L-lysine hydrochloride; organic acid salts such as L-lysine acetate and L-lysine malate; and the like. Specific examples of amino acid esters include L-tyrosine methyl ester, L-methionine methyl ester, L-methionine ethyl ester, and the like. Specific examples of N-acyl amino acids include N-acetyl-L-cysteine, N-acetyl-L-tryptophan, N-acetyl-L-proline, and the like. Specific examples of amino acid dipeptides include L-tyrosyl-L-tyrosine, L-alanyl-L-tyrosine, L-arginyl-L-tyrosine, L-tyrosyl-L-arginine, and the like. In particular, L-cysteine is preferably incorporated in the form of acetylcysteine, in view of stability. Such amino acids may be used singly, but are preferably used in a combination of two or more from the viewpoint of nutritional supplementation, for example, it is preferable to incorporate at least all of the essential amino acids (i.e., 9 types of amino acids: L-leucine, L-isoleucine, L-valine, L-lysine, L-threonine, L-tryptophan, L-methionine, L-phenylalanine, and L-histidine).

The second-chamber infusion comprises amino acids in a concentration of preferably 40 to 120 g/L, and more preferably 50 to 100 g/L, based on the total amount of free amino acids. In the infusion preparation of the present invention, the mixture of the first- and second-chamber infusions preferably has an amino acid concentration of 10 to 50 g/L, and more preferably 20 to 40 g/L, based on the total amount of free amino acids.

Preferable combinations of amino acids and their proportions in the second-chamber infusion are, for example, as follows in terms of free amino acids: L-leucine: 5 to 15 g/L; L-isoleucine: 3 to 9 g/L; L-valine: 3 to 9 g/L; L-lysine: 3 to 12 g/L; L-threonine: 1.2 to 6 g/L; L-tryptophan: 0.3 to 3 g/L; L-methionine: 0.6 to 4.6 g/L; L-phenylalanine: 1.3 to 9 g/L; L-cysteine: 0.1 to 1.8 g/L; L-tyrosine: 0.06 to 1.2 g/L; L-arginine: 3 to 12 g/L; L-histidine: 1.2 to 6 g/L; L-alanine: 3 to 9 g/L; L-proline: 1.2 to 6 g/L; L-serine: 0.6 to 4.2 g/L; glycine: 1.2 to 6 g/L; L-aspartic acid: 0.12 to 1.8 g/L; and L-glutamic acid: 0.12 to 1.8 g/L.

In the infusion preparation of the present invention, the mixture of the first- and second-chamber infusions preferably contains amino acids in the following concentrations in terms of free amino acids: L-leucine: 3 to 9 g/L; L-isoleucine: 1.5 to 4.5 g/L; L-valine: 1.5 to 4.5 g/L; L-lysine: 1.5 to 5 g/L; L-threonine: 0.6 to 3 g/L; L-tryptophan: 0.15 to 1.5 g/L; L-methionine: 0.3 to 2.4 g/L; L-phenylalanine: 0.85 to 4.5 g/L; L-cysteine: 0.03 to 0.9 g/L; L-tyrosine: 0.03 to 0.6 g/L; L-arginine: 1.5 to 5 g/L; L-histidine: 0.6 to 3 g/L; L-alanine: 1.5 to 4.5 g/L; L-proline: 0.6 to 3 g/L; L-serine: 0.3 to 2.1 g/L; glycine: 0.6 to 3 g/L; L-aspartic acid: 0.06 to 0.9 g/L; and L-glutamic acid: 0.06 to 0.9 g/L.

The electrolyte incorporated in the second-chamber infusion is an electrolyte that is used in the infusion field and serves as an active ingredient rather than an additive or the like. More specifically, the electrolyte is one contained in a body fluid (e.g., blood or intracellular fluid) (body fluid electrolyte), and can be referred to as a "physiologically important electrolyte." Specific examples of such electrolytes include potassium, calcium, sodium, magnesium, phosphorus, zinc, chlorine, and the like. In the infusion preparation of the present invention, the first-chamber infusion preferably does not comprise such an electrolyte. Potassium, in particular, is usually incorporated in both infusions of a two-chamber infusion preparation in order to avoid the risk of administering a high concentration of potassium; however, in the infusion preparation of the present invention, potassium is incorporated only in the second-chamber infusion.

Examples of calcium sources include calcium salts, such as calcium gluconate, calcium chloride, calcium glycerophosphate, calcium lactate, calcium pantothenate, calcium acetate, and the like. Calcium salts may be in the form of a hydrate (e.g., calcium gluconate hydrate). The second-chamber infusion comprises calcium in a concentration of preferably 1 or more, and more preferably 6 to 12 mEq/L. In the infusion preparation of the present invention, the mixture of first- and second-chamber infusions has a calcium concentration of 1 or more, preferably 1 or more and 9 mEq/L or less, and more preferably 3 to 6 mEq/L.

Examples of potassium sources include potassium chloride, potassium acetate, potassium citrate, potassium glycerophosphate, potassium sulfate, potassium lactate, and the like. Among these, potassium glycerophosphate is preferable because it also acts as a phosphorus source. Such potassium sources may be in the form of a hydrate. The second-chamber infusion comprises potassium in a concentration of preferably 40 mEq/L or less (more preferably 25 to 40 mEq/L). In the infusion preparation of the present invention, the mixture of the first- and second-chamber infusions has a potassium concentration of preferably 16 mEq/L or more, more preferably 16 to 25 mEq/L, and still more preferably 16 to 20 mEq/L.

Examples of sodium sources include sodium salts such as sodium chloride, sodium lactate, sodium acetate, sodium sulfate, sodium glycerophosphate, sodium citrate, and sodium lactate. When the infusion preparation of the present invention contains phosphorus and calcium and/or magnesium, it is preferable to use sodium citrate as (part of) the sodium sources in order to prevent, precipitation of these elements. Sodium sources may be in the form of a hydrate. The second-chamber infusion comprises sodium in a concentration of, for example, 50 to 100 mEq/L, and preferably 40 to 80 mEq/L. In the infusion preparation of the present invention, the mixture of the first- and second-chamber infusions has a sodium concentration of, for example, 25 to 50 mEq/L, and preferably 30 to 40 mEq/L.

Examples of magnesium sources include magnesium sulfate, magnesium chloride, magnesium acetate, and the like. Magnesium sources may be in the form of a hydrate. The second-chamber infusion comprises magnesium in a concentration of preferably 1 to 20 mEq/L, and more preferably 5 to 15 mEq/L. In the infusion preparation of the present invention, the mixture of the first- and second-chamber infusions preferably has a magnesium concentration of 0.5 to 10 mEq/L, and more preferably 2 to 6 mEq/L.

Preferable examples of phosphorus sources are organic salts, such as sodium glycerophosphate and potassium glycerophosphate, since the use of an inorganic salt as a phosphorus source may result in precipitation of calcium phosphate or magnesium phosphate. When lecithin is used as an emulsifying agent in the first chamber, the lecithin also acts as a phosphorus source. When phosphorus from the lecithin is present in a sufficient amount, it is unnecessary to add phosphorus to the second chamber, which is preferable since no precipitation of calcium phosphate etc. would occur. The second-chamber infusion contains phosphorus in a concentration of, for example, 0 to 20 mmol/L. In the infusion preparation of the present invention, the mixture of the first- and second-chamber infusions preferably has a phosphorus concentration of 1 to 20 mmol/L, and more preferably 5 to 10 mmol/L.

Examples of zinc sources include zinc sulfate, zinc chloride, and the like. Zinc sources may be in the form of a hydrate. The second-chamber infusion comprises zinc in a concentration of, for example, 2.5 to 15 µmol/L. In the infusion preparation of the present invention, the mixture of the first- and second-chamber infusions preferably has a zinc concentration of 1.5 to 9 µmol/L.

Examples of chlorine sources include sodium chloride, potassium chloride, magnesium chloride, calcium chloride, and the like. The second-chamber infusion comprises chlorine in a concentration of, for example, 50 to 100 mEq/L, and preferably 40 to 80 mEq/L. In the infusion preparation of the present invention, the mixture of the first- and second-chamber infusions preferably has a chlorine concentration of 25 to 60 mEq/L, and more preferably 30 to 40 mEq/L.

The pH of the second-chamber infusion may be optionally adjusted to 6.0 to 6.8, and preferably 6.2 to 6.7, by using a pH adjuster. The pH adjuster here may be the same as those mentioned above for the first-chamber infusion. When the second-chamber infusion has a pH within this range, amino acids that are prone to undergo chemical changes, such as L-cysteine and L-glutamic acid, can be stabilized. Furthermore, the pH of the mixture obtained by mixing the first-chamber infusion and second-chamber infusion can be maintained within the optimum range mentioned below.

Incorporation of at least one diprotic acid and/or tribasic acid selected from the group consisting of citric acid, malic acid, and succinic acid in the second-chamber infusion can inhibit the precipitation of calcium phosphate that occurs due to the formation of phosphoric acid, which is an impurity or a decomposition product of glycerophosphoric acid. In particular, citric acid is preferred as the diprotic acid and/or tribasic acid. The total concentration (mEq) of diprotic acids and tribasic acids in the second-chamber infusion is preferably equal to or more than the calcium concentration (mEq).

As a solvent in the second-chamber infusion as well, distilled water for injection can be typically used.

In the infusion preparation of the present invention, the second-chamber infusion has a relative osmotic pressure of about 2.0 to 3.5, and preferably about 2.0 to 3.0.

Further, the infusion preparation of the present invention may optionally contain a stabilizer. Examples of stabilizers that can be incorporated in the infusion preparation of the present invention include sulfites such as sodium bisulfite. To avoid decomposition of vitamin $B_1$ contained in the first-chamber infusion, sulfite is incorporated in the second-chamber infusion. The second-chamber infusion comprises sulfite in a concentration of, for example, 20 to 100 mg/L.

In addition to vitamin $B_1$, various types of vitamins can be added to the infusion preparation of the present invention. Various types of vitamins can be stably added to the infusion preparation in the two-chamber container without the need to place the infusion preparation in a three- or four-chamber container. This is one of the features of the infusion preparation of the present invention. Vitamins are classified into water-soluble vitamins and fat-soluble vitamins. In the infusion preparation of the present invention, a fat-soluble vitamin is added to the first-chamber infusion. Further, a water-soluble vitamin may be added to either the first- or second-chamber infusion. However, as described above, vitamin $B_1$ is added to the first-chamber infusion.

Examples of water-soluble vitamins added to the infusion preparation of the present invention include B-complex vitamins and vitamin C. In addition to vitamin $B_1$ (thiamine), examples of B-complex vitamins include vitamin $B_2$ (riboflavin), vitamin $B_3$ (niacin), vitamin $B_5$ (pantothenic acid), vitamin $B_6$, vitamin $B_7$ (biotin), vitamin $B_9$ (folic acid), vitamin $B_{12}$ (cyanocobalamin), and the like. Further, examples of fat-soluble vitamins include vitamin A, vitamin D (in particular, cholecalciferol), vitamin E, vitamin K, and the like.

Vitamin C (ascorbic acid), when used, can be added to the first- or second-chamber infusion, or both. However, it is preferably added to the second-chamber infusion. When vitamin C is added to the second-chamber infusion, the concentration of vitamin C in the second-chamber infusion is, for example, 50 to 500 mg/L, and preferably 100 to 400 mg/L. Further, in the infusion preparation of the present invention, the vitamin C concentration in the mixture of the first- and second-chamber infusions is preferably set to satisfy the following ranges: for example, 25 to 250 mg/L, preferably 50 to 200 mg/L, and more preferably 40 to 100 mg/L.

Usable vitamin $B_2$ includes riboflavin, riboflavin sodium phosphate, flavin mononucleotide, and the like. Vitamin $B_2$, when used, can be added to the first- or second-chamber infusion, or both. However, vitamin $B_2$ and folic acid are preferably placed in different chambers in order to prevent the destabilization of folic acid caused by a reaction between vitamin $B_2$ and folic acid. For example, when folic acid is added to the first-chamber infusion, vitamin $B_2$ is preferably added to the second-chamber infusion. When vitamin $B_2$ is added to the second-chamber infusion, the concentration of vitamin $B_2$ in the second-chamber infusion is, for example, 2.5 to 15 mg/L, and preferably 4 to 3 mg/L, on the riboflavin basis. Further, in the infusion preparation of the present invention, the vitamin $B_2$ concentration in the mixture of the first- and second-chamber infusions is preferably set to satisfy the following ranges: for example, 0.5 to 10 mg/L, and preferably 0.5 to 3 mg/L, on the riboflavin basis.

Usable vitamin $B_6$ include pyridoxine, salts of pyridoxine, such as pyridoxine hydrochloride, and the like. Vitamin $B_6$, when used, can be added to the first- or second-chamber infusion, or both. However, vitamin. Be becomes very unstable to light when it is present with vitamin $B_2$. Therefore, vitamin $B_6$ is preferably added to the infusion to which vitamin $B_2$ is not added. When vitamin $B_6$ is added to the first-chamber infusion, the concentration of vitamin $B_6$ in the first-chamber infusion is, for example, 2 to 10 mg/L, and preferably 2.5 to 6 mg/L, on the pyridoxine basis. Further, in the infusion preparation of the present invention, the vitamin $B_6$ concentration in the mixture of the first- and second-chamber infusions is preferably set to satisfy the following ranges: for example, 1 to 10 mg/L, and preferably 1.5 to 4.5 mg/L, on the pyridoxine basis.

Folic acid, when used, can be added to the first- or second-chamber infusion, or both; however, it is preferably added to the first-chamber infusion. When folic acid is added to the first-chamber infusion, the concentration of folic acid in the first-chamber infusion is, for example, 0.1 to 0.3 mg/L, and preferably 0.2 to 0.6 mg/L. Further, in the infusion preparation of the present invention, the folic acid concentration in the mixture of the first- and second-chamber infusions is preferably set to satisfy the following ranges: for example, 0.1 to 0.7 mg/L, and preferably 0.2 to 0.4 mg/L.

Usable vitamin $B_{12}$ includes cyanocobalamin, hydroxocobalamin acetate, methylcobalamin, and the like. Vitamin $B_{12}$, when used, can be added to the first- or second-chamber infusion, or both; however, it is preferably added to the first-chamber infusion when the second chamber contains sulfite. When vitamin $B_{12}$ is added to the first-chamber infusion, the concentration of vitamin $B_{12}$ in the first-chamber infusion is, for example, 2 to 10 μg/L, and preferably 2.5 to 6 μg/L. Further, in the infusion preparation of the present invention, the vitamin $B_{12}$ concentration in the mixture of the first- and second-chamber infusions is preferably set to satisfy the following ranges: for example, 0.5 to 10 mg/L, and preferably 0.5 to 3 mg/L.

As niacin, for example, nicotinamide is preferably used. Niacin, when used, can be added to the first- or second-chamber infusion, or both; however, it is preferably added to the second-chamber infusion. When niacin is added to the second-chamber infusion, the concentration of niacin in the second-chamber infusion is, for example, 10 to 100 mg/L, and preferably 20 to 50 mg/L. Further, in the infusion preparation of the present invention, the niacin concentration in the mixture of the first- and second-chamber infusions is preferably set to satisfy the following ranges: for example, 5 to 50 mg/L, and preferably 5 to 25 mg/L.

As pantothenic acid, panthenol is preferably used. Pantothenic acid, when used, can be added to the first- or second-chamber infusion, or both. When pantothenic acid is added to the first- or second-chamber infusion, the concentration of pantothenic acid is, for example, 5 to 30 mg/L, and preferably 10 to 20 mg/L, on the panthenol basis. Further, in the infusion preparation of the present invention, the panthenol concentration in the mixture of the first- and second-chamber infusions is set to satisfy the following ranges: for example, 2.5 to 15 mg/L, and preferably 5 to 10 mg/L.

Biotin, when used, can be added to the first- or second-chamber infusion, or both; however, it is preferably added to the second-chamber infusion. When biotin is added to the second-chamber infusion, the concentration of biotin in the second-chamber infusion is, for example, 10 to 100 μg/L, and preferably 20 to 80 μg/L. Further, in the infusion preparation of the present invention, the biotin concentration in the mixture of the first- and second-chamber infusions is preferably set to satisfy the following ranges: for example, 1 to 50 μg/L, and preferably 10 to 40 μg/L.

As vitamin A, retinol pa Imitate is preferably used. Further, vitamin A oil formed by dissolving retinol palmitate in oil can also be used. Vitamin A, which is fat-soluble, is added to the first-chamber infusion. The concentration of vitamin A in the first-chamber infusion is, for example, 1,000 to 5,000 IU/L, and preferably 2,000 to 4,000 IU/L. Further, in the infusion preparation of the present invention, the vitamin A concentration in the mixture of the first- and second-chamber infusions is preferably set to satisfy the following ranges: for example, 500 to 2,500 IU/L, and preferably 1,000 to 2,000 IU/L. "IU" stands for international unit. It is also called vitamin A unit.

As vitamin D, cholecalciferol (vitamin $D_3$) is preferably used. Vitamin D, which is fat-soluble, is added to the first-chamber infusion. The concentration of vitamin D in the first-chamber infusion is, for example, 2 to 10 μg/L, and preferably 2.5 to 6 μg/L. Further, in the infusion preparation of the present invention, the vitamin D concentration in the mixture of the first- and second-chamber infusions is preferably set to satisfy the following ranges: for example, 0.5 to 10 μg/L, and preferably 0.5 to 3 μg/L.

As vitamin E, tocopherol acetate is preferably used. Vitamin E, which is fat-soluble, is added to the first-chamber infusion. The concentration of vitamin E in the first-chamber infusion is, for example, 2 to 50 μg/L, and preferably 5 to 20 mg/L. Further, in the infusion preparation of the present invention, the vitamin E concentration in the mixture of the first- and second-chamber infusions is preferably set to satisfy the following ranges: for example, 1 to 25 mg/L, and preferably 2.5 to 10 mg/L.

As vitamin K, phytonadione (vitamin $K_1$) is preferably used. Vitamin K, which is fat-soluble, is added to the first-chamber infusion. The concentration of vitamin K in the first-chamber infusion is, for example, 50 to 2,500 μg/L, and preferably 80 to 2,000 μg/L. Further, in the infusion preparation of the present invention, the vitamin K concentration in the mixture of the first- and second-chamber infusions is preferably set to satisfy the following ranges: for example, 20 to 1,200 μg/L, and preferably 30 to 1,000 μg/L.

A preferable example of the active ingredients contained in the first- and second-chamber infusion compositions is shown below. At least one member selected from the group consisting of amino acids that have a buffer action, divalent organic acids, and trivalent organic acids is separately added to the first chamber.

First-Chamber Infusion
  Purified soybean oil: 10-50 g/L
  Glucose: 70-150 g/L
  Thiamine chloride hydrochloride: 3-10 mg/L
  Pyridoxine hydrochloride: 3-7 mg/L
  Cyanocobalamin: 2.5-5 μg/L
  Folic acid: 0.2-0.5 mg/L
  Vitamin A oil: 2,000-4,000 IU/L
  Cholecalciferol: 2.5-5 μg/L
  Tocopherol acetate: 5-20 mg/L
  Phytonadione: 80-2,000 μg/L
  Panthenol: 10-20 mg/L
Second-Chamber Infusion
  L-leucine: 5-15 g/L
  L-isoleucine: 3-9 g/L
  L-valine: 3-9 g/L
  L-lysine hydrochloride: 3.5-15 g/L
  L-threonine: 1.2-6 g/L
  L-tryptophan: 0.3-3 g/L
  L-methionine: 0.6-4.8 g/L
  Acetylcysteine: 0.13-2.4 g/L
  L-phenylalanine: 1.8-9 g/L
  L-tyrosine: 0.06-1.2 g/L
  L-arginine: 3-12 g/L
  L-histidine: 1.2-6 g/L
  L-alanine: 3-9 g/L
  L-proline: 1.2-6 g/L
  L-serine: 0.6-4.2 g/L
  Glycine: 1.2-6 g/L
  L-aspartic acid: 0.12-1.8 g/L
  L-glutamic acid: 0.12-1.8 g/L
  Sodium: 40-80 mEq/L
  Potassium: 25-40 mEq/L
  Calcium: 6-12 mEq/L Magnesium: 5-15 mEq/L
Chlorine: 40-80 mEq/L
Phosphorus: 0-20 mmoL/L
Zinc: 2.5-15 μmol/L
Riboflavin sodium phosphate: 5-10 mg/L
Ascorbic acid: 0.1-0.4 g/L
Biotin: 20-80 μg/L
Nicotinamide: 20-50 mg/L Both the first- and second-chamber infusions can be produced by a known method for producing infusions. For example, the first- and second-chamber infusions can be produced by dissolving each of the infusion components described above in distilled water for injection. Fat-soluble components are preferably used, for example, during emulsification as described above.

Mixture of the First- and Second-Chamber Infusions

At the time of use of the infusion preparation of the present invention, the first-chamber infusion and the second-chamber infusion are mixed. The mixture of the first- and second-chamber infusions has a pH of 6.53 or less, and preferably 6.4 or less. The pH of the mixture within this range, together with the features of the present invention, can achieve inhibition of the generation of unwanted insoluble matter after mixing of the two liquids in long-term storage. More specifically, first, the other features of the present invention achieve inhibition of the formation of free fatty acids in the first-chamber infusion during long-term storage. Further, by adjusting the pH of the mixture within the above range, the generation of unwanted insoluble matter in the mixture due to the presence of free fatty acids is inhibited.

Accordingly, to ultimately inhibit the generation of unwanted insoluble matter, it is important to effectively combine other features of the present invention, in particular, a feature that the first-chamber infusion comprises at least one member selected from the group consisting of amino acids that have a buffer action, divalent organic acids, and trivalent organic acids, such as histidine, in a total concentration of 0.15 g/L or more; and a feature that the mixture has a pH of 6.53 or less. In this sense, it is sufficient when the first-chamber infusion comprises at least one member selected from the group consisting of amino acids that have a buffer action, divalent organic acids, and trivalent organic acids in a total concentration of 0.15 g/L or more, and the mixture has a pH of 6.53 or less. It is preferable that (1) the first-chamber infusion comprises at least one member selected from the group consisting of amino acids that have a buffer action, divalent organic acids, and trivalent organic acids in a total concentration of 0.3 g/L or mere, and the mixture has a pH of 6.53 or less; or (2) the first-chamber infusion comprises at least one member selected from the group consisting of amino acids that have a buffer action, divalent organic acids, and trivalent organic acids in a total concentration of 0.2 g/L or mere, and the mixture has a pH of 6.4 or less.

The present inventors found that free fatty acids generate unwanted insoluble matter in the mixture specifically when free fatty acids form a salt with $Ca^{2+}$. Therefore, to ultimately inhibit the generation of unwanted insoluble matter, the $Ca_{2+}$ concentration is preferably reduced in the mixture of the first- and second-chamber infusions, and the $Ca^{2+}$ concentration is preferably 3 to 6 mEq/L in the mixture of the first- and second-chamber infusions.

The infusion preparation of the present invention has a titratable acidity of preferably 1 to 10 and a relative osmotic pressure of preferably 2 to 3.

Further, in the infusion preparation of the present invention, the volume ratio between the first-chamber infusion and the second-chamber infusion is suitably determined according to, for example, the fluid volumes of the first- and second-chamber infusions described above. In view of the stability of each component and the osmotic pressure setting in each chamber, the volume ratio (first-chamber infusion: second-chamber infusion) is, for example, 3:2-3:5.

Further, the calorific value of the mixture is preferably 450 to 750 kcal/L, and more preferably 500 to 650 kcal/L. In this calorific value, the percentage of fat is preferably 40% or less, and more preferably 20 to 40%. Further, in this calorific value, the percentages of sugar, fat, and amino acid are preferably as follows: 40 to 60% sugar, 20 to 40% fat, and 10 to 30% amino acid, and more preferably, 45 to 55% sugar, 25 to 35% fat, and 15 to 25% amino acid. An approximate calorific value of each component, can be determined by multiplying the amount (g) by 4 for sugar, by 9 for fat, and by 4 for amino acid. Specifically, the calorific value of sugar is about 4 kcal/g, the calorific value of fat is about 9 kcal/g, and the calorific value of amino acid is about 4 kcal/g. An approximate calorific value can be determined based on this information. The calorific value of the mixture described above is based on the value calculated accordingly.

A preferable example of the composition of each component in the mixture is shown below.

TABLE 1

| | | | |
|---|---|---|---|
| Electrolytes | Na | 35 | mEq |
| | K | 20 | mEq |
| | Mg | 5 | mEq |
| | Ca | 5 | mEq |
| | Cl | 35 | mEq |
| | P | 10 | mmol |
| | Zn | 5 | μmol |
| Sugar | Glucose | 75 | g |
| Fat | Purified soybean oil | 20 | g |
| Amino acid | Amino acid | 30 | g |
| Vitamins | Thiamine chloride hydrochloride | 1.9 | mg |
| | Riboflavin sodium phosphate | 2.3 | mg |
| | Pyridoxine hydrochloride | 2.45 | mg |
| | Cyanocobalamin | 2.5 | μg |
| | Nicotinamide | 20 | mg |
| | Panthenol | 7 | mg |
| | Folic acid | 0.2 | mg |
| | Biotin | 30 | μg |
| | Ascorbic acid | 50 | mg |
| | Vitamin A oil | 1,650 | IU |
| | Cholecalciferol | 2.5 | μg |
| | Tocopherol acetate | 5 | mg |
| | Phytonadione | 1 | mg |
| Additives | Egg yolk lecithin | 2.4 | g |
| | L-histidine | 0.2 | g |

Infusion Preparation Usage Form

The infusion preparation of the present invention is used in order to manage the nutrition of a perioperative patient when the patient has mild hyperproteinemia or mild malnutrition due to inadequate oral intake or when the patient is in the invasive phase. In particular, the infusion preparation is suitably used to manage the nutrition of a patient having difficulty receiving oral nutritional support in the postoperative period or due to a digestive disorder and the like (preferably, a patient who has undergone gastric resection surgery). The infusion preparation of the present invention is administered to a patient for 1 to 14 days after surgery, and preferably 1 to 3 days after surgery. The nutritional status of the patient can thereby be maintained in a healthy state. The dose and the dosing rate can be suitably determined in view of each patient's symptoms, age, and the like. In particular, when the infusion preparation of the present invention is used, the infusion preparation can maintain, by itself, the nutritional status of the patient in a healthy state for the duration of administration.

The infusion preparation of the present invention is preferably administered into a peripheral vein. In other words, the infusion preparation of the present invention is preferably an infusion preparation for peripheral intravenous administration. In general, administration of an infusion that has overly high osmotic pressure into a peripheral vein can cause vascular pain or phlebitis. However, there is no such risk when the infusion preparation of the present invention is used. Therefore, the effect of the infusion preparation of the present invention is suitably demonstrated when the infusion preparation is administered into a peripheral vein.

Infusion Container

The container in which the first-chamber infusion and the second-chamber infusion are placed is not particularly limited insofar as the container has two chambers that are intercommunicable. Examples include two-chamber containers (infusion bags) in which the chambers are separated by a partition wall that can be communicably opened, such as ones in which a partition wall is formed by an easily peelable seal (Japanese Unexamined Patent Publication No. H2-4671, Japanese Unexamined Utility Model Publication No. H5-5133, and the like), ones in which a partition wall is formed by clipping the space between the chambers (Japanese Unexamined Patent Publication No. S63-309263 and the like), and ones in which various communicating means that can open the partition wall is provided to the partition wall (Japanese Examined Patent Publication No. S63-20550 and the like). Of these, an infusion bag in which the partition wall is formed by an easily peelable seal is preferable because it is suitable for mass production and the chambers can be easily brought into communication. Further, various gas-permeable plastics commonly used for medical containers are used as materials of the above container. Examples include flexible plastics, such as polyethylene, polypropylene, polyvinyl chloride, crosslinked ethylene-vinyl acetate copolymer, ethylene-α-olefin copolymer, blends of such polymers, and laminates comprising such polymers.

The first- and second-chamber infusions can be filled and packaged in the container by a conventional method. For example, the chambers are filled with the infusions under an inert gas atmosphere, sealed, and sterilized by heat.

Heat sterilization can be performed by a known method, such as high-pressure steam sterilization or hot water shower sterilization. If necessary, the heat sterilization can be carried out in an inert gas atmosphere such as carbon dioxide or nitrogen. The infusion preparation of the present invention does not generate unwanted insoluble matter even when sterilized in high-pressure steam at 116 to 121° C.

Further, the first- and second-chamber infusions contained in the container are preferably packaged together with a deoxidant in an oxygen barrier exterior bag in order to reliably prevent deterioration, oxidation, etc. In particular, when an infusion bag in which the partition wall is formed by an easily peelable seal is used as a container, the infusion bag is preferably packaged in such a manner that the infusion bag is folded, for example, in half, at the easily peelable seal portion to prevent the partition wall from being communicably opened by external pressure. Further, for example, filling and packaging may be optionally performed with an inert gas.

Commonly or widely used films, sheets, and the like formed from various materials can be used as materials of the oxygen barrier exterior bag suitable for the package. Specific examples include ethylene vinylalcohol copolymer, polyvinylidene chloride, polyacrylonitrile, polyvinyl alcohol, polyamide, polyester, and the like. Examples also include films and sheets formed from materials comprising at least one of these materials.

Usable deoxidants include various known deoxidants, such as those comprising, as an active ingredient, ferric hydroxide, ferric oxide, iron carbide, or other iron compounds, and those comprising low-molecular-weight phenol and activated carbon. Examples of product names of typical commercial products include Ageless (produced by Mitsubishi Gas Chemical), Moduran (produced by Nippon Kayaku), Secur (produced by Nippon Soda), Tamotsu (produced by Oji Kako), Keepit (produced by Drency), and the like.

EXAMPLES

The present invention is described in more detail below with reference to Examples. The invention, however, is not limited to the following Examples.

Production of Infusion Preparations

1. Production of First-Chamber Infusions 1 to 4

Purified soybean oil, purified egg yolk lecithin, and glucose in the amounts shown in Table 2 were added to water. The resulting mixture was subjected to crude emulsification using a homomixer. The resulting crude emulsion was then subjected to fine emulsification using a high-pressure emulsifier (Manton-Gaulin). Further, L-histidine in the amounts shown in Table 2 and water were added thereto to make the total volume of each emulsion 300 mL. Further, hydrochloric acid was used to adjust the pH. The first-chamber infusions thus obtained had a relative osmotic pressure of 2.9 and a titratable acidity of 1.

TABLE 2

|  | Formulation 1 | Formulation 2 | Formulation 3 | Formulation 4 |
| --- | --- | --- | --- | --- |
| Purified soybean oil | | 10 g | | |
| Glucose | | 37.5 g | | |
| Purified egg yolk lecithin | | 1.2 g | | |
| L-histidine | 0.03 g | 0.06 g | 0.09 g | 0.15 g |
| pH | 6.3 | 6.3 | 6.3 | 6.3 |

2. Formulation of Second-Chamber Infusions A to D

Amino acids, electrolytes, and a stabilizer (sodium hydrogen sulfite) in the amounts shown in Table 3 were dissolved in distilled water for injection to prepare an amino acid electrolyte solution. Further, the pH of the electrolyte solution was adjusted to the levels shown in Table 3 with glacial acetic acid, and the total volume of each solution was adjusted to 250 mL, giving second-chamber infusions. The second-chamber infusions thus obtained had a relative osmotic pressure of 2.7. The second-chamber infusions had a citric acid concentration of 12.68 mEq/L and a calcium concentration of 10.00 mEq/L.

TABLE 3

|  | Formulation A | Formulation B | Formulation C |
| --- | --- | --- | --- |
| L-leucine | | 2.100 g | |
| L-isoleucine | | 1.200 g | |
| L-valine | | 1.200 g | |

TABLE 3-continued

|  | Formulation A | Formulation B | Formulation C |
|---|---|---|---|
| L-lysine hydrochloride |  | 1.965 g |  |
| L-threonine |  | 0.855 g |  |
| L-tryptophan |  | 0.300 g |  |
| L-methionine |  | 0.585 g |  |
| Acetylcysteine |  | 0.202 g |  |
| L-phenylalanine |  | 1.050 g |  |
| L-tyrosine |  | 0.075 g |  |
| L-arginine |  | 1.575 g |  |
| L-histidine |  | 0.750 g |  |
| L-alanine |  | 1.200 g |  |
| L-proline |  | 0.750 g |  |
| L-serine |  | 0.450 g |  |
| Glycine |  | 0.885 g |  |
| L-aspartic acid |  | 0.150 g |  |
| L-glutamic acid |  | 0.150 g |  |
| Sodium chloride |  | 0.215 g |  |
| Potassium chloride |  | 0.220 g |  |
| Sodium citrate hydrate |  | 0.311 g |  |
| Sodium L-lactate solution (60%) (as sodium L-lactate) |  | 1.967 g (1.180 g) |  |
| 50% potassium glycerophosphate solution (as potassium glycerophosphate) |  | 1.750 g (0.875 g) |  |
| Calcium gluconate hydrate |  | 0.561 g |  |
| Magnesium sulfate hydrate |  | 0.309 g |  |
| Zinc sulfate hydrate |  | 0.72 mg |  |
| Sodium bisulfite |  | 12.5 mg |  |
| pH | 6.5 | 6.7 | 6.9 |

3. Filling and Packaging

Using two-chamber polyethylene containers with the chambers being partitioned by an easily peelable seal, formulations 1 to 4 were placed as the first-chamber infusion in the lower chambers of the containers, whereas formulations A to C were placed as the second-chamber infusion in the upper chambers of the containers. After the atmosphere in the vacant space of each chamber was replaced with nitrogen gas and each container was sealed, high-pressure steam sterilization was performed at a temperature of 116° C. for 26 minutes. Each container was then folded at the easily peelable seal portion, and enclosed with a deoxidant in an exterior bag made of gas barrier film, thus obtaining an infusion preparation. Three preparations of the same infusion were prepared for each type.

The infusion preparations obtained above, containing formulations 1 to 4 as the first-chamber infusion and formulation A as the second-chamber infusion, were stored at 60° C./75% RH for 3 weeks, and then the first-chamber infusion and second-chamber infusion were mixed. Whether unwanted insoluble matter was generated was confirmed immediately after mixing, 26 hours after mixing, and 48 hours after mixing. The pH was measured 48 hours after mixing. Table 4 shows the results.

Whether free fatty acids were formed was visually evaluated according to the following criteria.

A: No unwanted insoluble matter was observed on the inner surface of the container.

B: White unwanted insoluble matter was observed on the inner surface of the container.

татBLE 4

| Upper chamber: second-chamber infusion (pH) | Lower chamber: first-chamber infusion (amount of L-histidine added) | Round of tests | Confirmation on generation of unwanted insoluble matter Measurement time | | | |
|---|---|---|---|---|---|---|
| | | | Immediately after mixing | 26 hours after mixing | 48 hours after mixing | pH |
| Formulation A (pH 6.5) | Formulation 1 (0.1 g/L) | 1st | A | B | B | 6.40 |
| | | 2nd | A | B | B | 6.39 |
| | | 3rd | A | B | B | 6.40 |
| | Formulation 2 (0.2 g/L) | 1st | A | A | A | 6.41 |
| | | 2nd | A | A | A | 6.40 |
| | | 3rd | A | A | A | 6.41 |
| | Formulation 3 (03 g/L) | 1st | A | A | A | 6.39 |
| | | 2nd | A | A | A | 6.40 |
| | | 3rd | A | A | A | 6.39 |
| | Formulation 4 (0.5 g/L) | 1st | A | A | A | 6.37 |
| | | 2nd | A | A | A | 6.37 |
| | | 3rd | A | A | A | 6.38 |

When the infusion preparation comprised formulation 1 containing L-histidine in a concentration of 0.1 g/L as the first-chamber infusion/white unwanted insoluble matter started to be observed on the inner surface of the containers containing the preparation 26 hours after mixing.

The infusion preparations obtained above, each containing one of formulations 1 to 4 as the first-chamber infusion and containing formulation B as the second-chamber infusion, were stored at 60° C./75% RH for 3 weeks, and then the first-chamber infusion and the second-chamber infusion were mixed. Whether unwanted insoluble matter was generated was confirmed immediately after mixing, 26 hours after mixing, and 48 hours after mixing. The pH was measured 48 hours after mixing. Table 5 shows the results.

Whether free fatty acids were formed was confirmed in the same manner as described above.

TABLE 5

| Upper chamber: second-chamber infusion (pH) | Lower chamber first-chamber infusion (amount of L-histidine added) | Round of tests | Confirmation on generation of unwanted insoluble matter Measurement time | | | |
|---|---|---|---|---|---|---|
| | | | Immediately after mixing | 26 hours after mixing | 48 hours after mixing | pH |
| Formulation B (pH 6.7) | Formulation 1 0.03 g/L | 1st | A | B | B | 6.53 |
| | | 2nd | A | B | B | 6.53 |
| | | 3rd | A | B | 8 | 6.53 |
| | Formulation 2 0.03 g/L | 1st | A | B | B | 6.54 |
| | | 2nd | A | B | B | 6.55 |
| | | 3rd | A | B | B | 6.54 |
| | Formulation 3 0.03 g/L | 1st | A | A | A | 6.53 |
| | | 2nd | A | A | A | 6.53 |
| | | 3rd | A | A | A | 6.53 |
| | Formulation 4 (0.03 g/L) | 1st | A | A | A | 6.51 |
| | | 2nd | A | A | A | 6.52 |
| | | 3rd | A | A | A | 6.52 |

When the infusion preparation comprised formulation 1 containing L-histidine in a concentration of 0.1 g/L as the first-chamber infusion, white unwanted insoluble matter started to be observed on the inner surface of the containers containing the preparation 26 hours after mixing. Further, when the infusion preparation comprised formulation 2 and formulation B and had a pH of 6.54 or 6.55 after mixing, white unwanted insoluble matter started to be observed on the inner surface of the containers containing the mixture of formulation 2 and formulation B 26 hours after mixing.

The infusion preparations obtained above, each containing one or formulations 1 to 4 as the first-chamber infusion and formulation C as the second-chamber infusion, were stored at 60° C./75% RH for 3 weeks, and then the first-chamber infusion and the second-chamber infusion were mixed. Whether unwanted insoluble matter was generated was confirmed immediately after mixing, 26 hours after mixing, and 43 hours after mixing. The pH was measured 48 hours after mixing. Table 6 shows the results.

Whether free fatty acids were formed was confirmed in the same, manner as described above.

TABLE 6

| Upper chamber: second-chamber infusion (pH) | Lower chamber first-chamber infusion (amount of L-histidine added) | Round of tests | Confirmation on generation of unwanted insoluble matter Measurement time | | | pH |
|---|---|---|---|---|---|---|
| | | | Immediately after mixing | 26 hours after mixing | 48 hours after mixing | |
| Formulation C (pH 6.9) | Formulation 1 (0.03 g/ 300 mL) | 1st | A | B | B | 6.66 |
| | | 2nd | A | B | B | 6.68 |
| | | 3rd | A | B | B | 6.68 |
| | Formulation 2 (0.06 g/ 300 mL) | 1st | A | B | B | 6.67 |
| | | 2nd | A | B | B | 6.68 |
| | | 3rd | A | B | B | 6.68 |
| | Formulation 3 (0.09 g/ 300 mL) | 1st | A | B | B | 6.68 |
| | | 2nd | A | B | B | 6.68 |
| | | 3rd | A | B | B | 6.68 |
| | Formulation 4 (0.15 g/ 300 mL) | 1st | A | B | B | 6.65 |
| | | 2nd | A | B | B | 6.65 |
| | | 3rd | A | B | B | 6.65 |

Forty-eight hours after mixing, all of the infusion preparations containing formulation C having a pH of 6.9 as the second-chamber infusion had a pH higher than 6.53, no matter which of formulations 1 to 4 was used as the first-chamber infusion. Further, white unwanted insoluble matter started to be observed on the inner surface of the containers 26 hours after mixing.

The invention claimed is:

1. An infusion preparation comprising two chambers separated by a communicably openable partition,
    a first chamber containing a first-chamber infusion comprising a fat emulsion and further comprising at least one member selected from the group consisting of amino acids that have a buffer action, divalent organic acids, and trivalent organic acids,
    a second chamber containing a second-chamber infusion comprising an amino acid and at least calcium as an electrolyte, wherein
    a total concentration of the amino acids that have a buffer action, divalent organic acids, and trivalent organic acids in the first-chamber infusion is 0.15 to 0.5 g/L, and
    a mixture of the first- and second-chamber infusions has a pH of 6.53 or less as measured 48 hours after the partition is communicably opened.

2. The infusion preparation according to claim 1, wherein the fat emulsion comprises an emulsifying agent, and the first-chamber infusion comprises the emulsifying agent in a concentration of 0.01 to 2 w/v %.

3. The infusion preparation according to claim 1, wherein the mixture of the first- and second-chamber infusions after the partition is communicably opened contains $Ca^{2+}$ in a concentration of 1 mEq/L or more.

4. The infusion preparation according to claim 1, wherein the second-chamber infusion further comprises at least citric acid as the electrolyte, and the second-chamber infusion has a citric acid concentration (mEq) equal to or more than the calcium concentration (mEq).

5. The infusion preparation according to claim 1, wherein the first-chamber infusion comprises at least histidine as the amino acids that have a buffer action.

6. A mixture of the first- and second-chamber infusions of claim 1 obtained by communicably opening the partition.

* * * * *